United States Patent [19]

Martinelli et al.

[11] Patent Number: 4,821,731
[45] Date of Patent: Apr. 18, 1989

[54] ACOUSTIC IMAGE SYSTEM AND METHOD

[75] Inventors: Michael A. Martinelli, Winchester; Peter von Thuna, Lexington, both of Mass.

[73] Assignee: Intra-Sonix, Inc., Burlington, Mass.

[21] Appl. No.: 129,830

[22] Filed: Dec. 8, 1987

Related U.S. Application Data

[63] Continuation-in-part of Ser. No. 856,621, Apr. 25, 1986, abandoned.

[51] Int. Cl.⁴ .............................................. A61B 10/00
[52] U.S. Cl. .......................... 128/662.06; 128/660.03; 128/653
[58] Field of Search .............. 128/653, 654, 656, 660, 128/661

[56] References Cited

U.S. PATENT DOCUMENTS

| | | | |
|---|---|---|---|
| RE30397 | 9/1980 | King | 128/660 |
| 3,565,062 | 2/1971 | Kuris | 128/24 |
| 3,690,311 | 9/1972 | Schorum | 128/2 V |
| 3,868,565 | 2/1975 | Kuipers | 324/34 R |
| 3,938,502 | 2/1976 | Bom | 128/2 V |
| 4,207,874 | 6/1980 | Choy | 128/6 |
| 4,315,514 | 2/1982 | Drewes | 128/653 |
| 4,317,078 | 2/1982 | Weed et al. | 128/653 X |
| 4,349,032 | 9/1982 | Koyata | 128/660 |
| 4,375,818 | 3/1983 | Suwaki et al. | 128/660 |
| 4,391,282 | 7/1983 | Ando, et al. | 128/660 |
| 4,419,987 | 12/1983 | Ogiu | 128/4 |
| 4,448,201 | 5/1984 | Matsumoto | 128/660 |
| 4,459,990 | 7/1984 | Barnea | 128/656 |
| 4,462,408 | 7/1984 | Silverstein | 128/660 |
| 4,489,728 | 12/1984 | Matsuo et al. | 128/660 |
| 4,494,549 | 1/1985 | Namba et al. | 128/660 |
| 4,556,057 | 12/1985 | Hiruma et al. | 128/303.1 |
| 4,571,750 | 2/1986 | Barry | 623/258 |
| 4,572,198 | 2/1986 | Codrington | 128/653 |
| 4,576,177 | 3/1986 | Webster, Jr. | 128/660 |
| 4,587,972 | 5/1986 | Morantte | 128/660 |
| 4,589,419 | 5/1986 | Laughlin, et al. | 128/663 |
| 4,669,465 | 5/1987 | Moore, et al. | 128/303.1 |
| 4,674,515 | 6/1987 | Andou | 128/660 |
| 4,697,595 | 10/1987 | Breyer et al. | 128/611 X |

Author & Date unknown—Transducer Motion Mechanization, "Synchros and Resolvers", pp. 56–67.

Primary Examiner—Francis Jaworski
Attorney, Agent, or Firm—Schiller, Pandiscio and Kusmer

[57] ABSTRACT

An apparatus and method is disclosed for imaging internal features of a living body at a preselected site so that the data can be imaged in a quick, efficient and reliable manner with high resolution. The apparatus includes a catheter having a longitudinal axis, a proximal end and a distal end such that the catheter is adapted to be partially inserted into said living body so that said distal end is positioned relative to the preselected site and imaging data relating to the internal features can be acoustically provided at said distal end by moving said distal end through a plurality of positions relative to the site and generating an acoustic signal when the distal end is at each of said positions. The acoustic energy responsive to each acoustic signal at each of the positions is sensed so as to create a set of data. The location, including the orientation of said distal end of said catheter is sensed at each of said positions. The sets of data and the respective positions from which each was obtained is related to one another so as to create an image of the internal features of the body.

48 Claims, 7 Drawing Sheets

ACOUSTIC IMAGE SYSTEM AND METHOD

This application is a continuation-in-part of my prior, co-pending application, U.S. Ser. No. 856,621, filed Apr. 25, 1986 in the name of Michael A. Martinelli, Thomas Aretz, John R. Butterly and Stanley M. Shapshey (hereinafter referred to as the "Parent Application"), now abandoned in favor of continuation application U.S. Ser. No. 217,053 filed July 8, 1988.

The present invention relates generally to acoustical imaging of internal features of a living body or the like, and more specifically to an improved device for accurately moving and positioning an image sensing device in the living body so that imaging information can be derived at a predetermined site with sufficiently high resolution.

Devices are known for using an acoustic pulse to generate echo sounds relating to internal features of various parts of a living body. Such devices, for example the one described in U.S. Pat. No. 4,576,177 (hereinafter referred to as the "Webster Patent"), include an electro-acoustical transducer device positioned on the tip section of a catheter so that the transducer device can be inserted into a liquid-filled or fillable body canal or cavity. The catheter is moved into position at the particular site of the body so that the transducer device generates each acoustic pulse in the direction of interest.

The transducer device of the Webster Patent provides an acoustic output pulse and receives return pulses, i.e., echoes, from surface discontinuies in the form of impedance mismatches (at the ultrasonic frequency) of the precise part of the body at which the pulse is directed. The temporal character of the echo pulses, in response to the initial pulse, returning from the direction of propagation of the initial pulse provides information about the tissue through which the pulses travel. More specifically, the relative timing of the return pulses corresponding to impedance discontinuities provides information on the thickness of various types of tissue (e.g., fat, arteriosclerotic plaque, etc.) at the specific location at which the initial pulse is directed. The relative strength of such echoes reflects the differences in impedance between adjacent boundaries of the different types of tissue, and therefore the difference in densities of the material. The acoustic technique can therefore be used to ascribe a signature for each type and character of tissue from which echoes are received.

As described in both the Parent Application and the Webster Patent, acoustically derived information can be particularly useful in such procedures as removing arteriosclerotic plaque deposits which restrict the flow of blood in coronary arteries. By moving the distal end of a catheter to the location of the diseased site, laser radiation can be directed through an optical fiber, provided within the catheter, onto the plaque with sufficient intensity so as to vaporize the plaque. The plaque thus can be removed without the trauma associated with open heart surgery. However, such a procedure requires specific knowledge of the location, thickness and density of the plaque to be removed in order to minimize damage to the arterial wall at the diseased site. As described in both the Webster patent and the Parent Application, the use of acoustically derived information is advantageous since it can provide such information better than other known techniques.

For example, X-ray fluoroscopy can be used to position the catheter. However, the latter technique (a) requires the injection of a radiopaque material into the occluded blood vessel, and (b) viewing the X-ray shadow images of the artery and the catheter with a fluoroscope. Although helpful in generally locating the area of interest, X-ray fluoroscopy yields images of poor resolution and incomplete information on the thickness and density of the plaque deposits. Further, real time data is difficult, if not impossible to obtain using X-ray fluoroscopy during the laser vaporization step of the procedure.

As indicated in the Webster Patent, fiberoptic scopes, having illumination and direct optical viewing capabilities which can be used to inspect the diseased site. However, such devices require the user to block the blood flow through the blood vessel and to subsequently flush the blood vessel with a clear liquid such as saline, until a clear optical viewing path is achieved. Not only does the use of fiberoptic scopes require the stoppage of blood flow, but also prevents direct viewing during the laser vaporization step and provides inadequate information on the density and thickness of the plaque. As a result the chance that the arterial wall will be damaged is greatly increased.

The system described in the Webster Patent provides at any one time only the information relating to the set of echoes received in response to a pulse transmitted in a preselected direction. There is no attempt to relate any of the information obtained from one set of echoes to any other set of echoes taken from another position of the transducer device at the site where the information is being obtained. This provides a very limited "view" of the area from which the information is being obtained (restricted by the "angle of view" of the transducer device), and prevents the surgeon from knowing the nature of the surrounding tissue which is not within the angle of view when the data is obtained in response to an acoustic pulse. As a result more time must be spent after each application of the laser at the specific location being viewed in order to try to locate another location at the site containing diseased tissue.

It is a principal object of the present invention therefore, to provide a system for and method of collecting sets of data derived from acoustic signals generated at a corresponding plurality of locations at the diseased site and to relate the sets of data with respect to the relative locations from which the sets of data are obtained so that the data can be used to create a coherent image of the diseased site.

For example, as will be more evident hereinafter, in accordance with the present invention in order to create an image of an artherosclerotic lesion on the interior wall of an artery, one can longitudinally as well as rotatably displace the catheter tip (and thus the transducer device on the catheter tip) through a predefined diseased site so that a set of return pulses is obtained from each location within the diseased site. The set of return pulses obtained for each angular and longitudinal position of the catheter then can be related to one another so as create relative spatial information of the structure of the portions of the diseased site represented by the sets of return pulses based on known signatures of various types of tissue encountered in such diseased sites. Alternatively, the sets of return pulses can be related to one another as a function of the relative spatial positions from which the sets of return pulses are obtained so as to create a three-dimensional presentation of the diseased site, as described and illustrated in the Parent Application.

Devices for determining the position of the tip section of a catheter are known. In U.S. Pat. No. 4,173,228 (Van Steenwyk et al.) the tip of a catheter positioned in the body can be detected electromagnetically by disposing a coupling coil in the tip of the catheter coaxially with the longitudinal axis of the catheter at the tip. Leads from the coil extend along the catheter to an external receiving circuit. A "search probe" includes a pair of coils mounted perpendicular to one another. The probe is positioned outside the body. A voltage is applied to one of the probe coils so that an electromagnetic field is generated through the body and a voltage induced in the catheter coil. This voltage is sensed by the receiving circuit. The induced signal is maximized when the axes of the probe and catheter coils are parallel and the coils are laterally or axially aligned. The signal is minimized when coil axes are disposed perpendicular with respect to one another. The relative phase of the transmitted and received signals indicates whether the energized probe coil and catheter coil are facing in the same or opposite directions, and thus determines the direction in which the catheter tip is pointing.

In operation, one probe coil is energized and the probe is moved by the physician until a maximum signal is detected and the position of the probe and orientation of the energized probe coil is indicated on the patient's skin. The first probe coil is then deenergized while the second probe coil is energized with the probe positioned in the same location which produced the maximum signal in the first scan.

If the detected signal is insignificant, the catheter-tip position determined in the first scan is accurate, and the center of the catheter coil is directly below the mark, with the catheter tip pointing in a plane parallel to the plane of the first probe coil. If a significant signal is noted when the second probe coil is energized, a second scan is made to determine a new position of maximum coupling is indicated by a peak in the detected signal. The patient's skin is again marked. The position of the catheter tip will lie beneath a line connecting the first and second marks made on the skin. Both probe coils are then energized and the probe moved along the line connecting the two marks. A dip or peak in the detected signal will then indicate the position of the catheter tip. A dip in signal strength shows that the catheter tip is pointing away from the probe, and a peak shows the tip is pointing toward the probe. The procedure is repeated as many times as necessary during catheter insertion to insure that the catheter tip is following a desired path.

As described in the Van Steenwyk et al patent the tip position of a fully inserted catheter can be constantly monitored if desired by taping one or more transmission coils to the patient's skin directly over the catheter coil and then noting any change in the output reading of the catheter coil. In addition, the catheter tip can also be sensed by using sonic energy propagated through the body and sensed by an acoustic transducer at the catheter tip and wired to an external circuit. Further, three or more coils may be used in an array and driven at different frequencies for external discrimination to enable a more rapid determination of catheter tip position.

The system described by Van Steenwyk et al does not include means for imaging the internal features of a human body, for example, of a coronary artery, particularly on the detailed level required for ablating arteriosclerotic plaque from the walls of those blood vessels. For one, the device is not constructed to acquire image data relating to the thickness and types of tissue present at a diseased site, which is necessary to reliably perform the ablating procedure. The system is designed solely to locate the tip of a catheter in the body.

In order to obtain images appropriate for ablating atherosclerotic plaque, the angular orientation and position of the transducer device used for receiving the sets of acoustically derived data must be known at the time the corresponding sets are obtained. It is clear that the Van Steenwyk et al. system is incapable of determining the angular orientation of the tip end of the catheter.

Accordingly, it is another object of the present invention to provide a system for and method of acquiring ultrasonic echo data so as to create a relatively high resolution image of a predetermined site within a living body in a quick and dependable manner.

And another object of the present invention is to provide a system for and method of determining the relative position of the tip of a catheter within a living body, as well as the relative angular orientation of transducer device positioned on the tip of the catheter about the longitudinal axis of the catheter.

The foregoing and other objects will be achieved by an improved apparatus for imaging internal features of a living body within a preselected site, wherein the apparatus comprises, in combination:

a catheter having a longitudinal axis, a proximal end and a distal end such that said catheter is adapted to be partially inserted into said living body so that said distal end is positioned relative to said preselected site so that said imaging information of said internal features can be acoustically sensed at said distal end;

image data sensing means, coupled to said catheter at said distal end, for acoustically sensing said imaging information of said body in the general direction of an image data sensing axis transverse to the longitudinal axis of said catheter at said distal end so that rotation of said catheter about said longitudinal axis rotates said image data sensing axis about said longitudinal axis; and position sensing means for determining externally of said body the position of said imaging data sensing means within said body and the angular orientation of said image data sensing axis about said longitudinal axis.

In accordance with another aspect of the present invention the apparatus comprises, in combination:

a catheter having a longitudinal axis, a proximal end and a distal end such that said catheter is adapted to be partially inserted into said living body so that said distal end is positioned relative to said preselected site and imaging data relating to said internal features can be acoustically provided at said distal end by moving said distal end through a plurality of positions relative to said site and generating an acoustic signal when said distal end is at each of said positions;

means for selectively generating said acoustic signal when said distal end is at earth of said positions;

first sensing means for sensing acoustic energy in response to said acoustic signal at each of said positions;

second sensing means for sensing the location of said distal end of said catheter at each of said positions;

means, responsive to said first and second sensing means, for collecting a set of data derived from the acoustic energy sensed by said sensing means at each of said positions and corresponding information relative to the corresponding position from which each set of data is obtained so as to form a plurality of said sets corresponding to a plurality of said positions; and means for relating the plurality of sets of data with respect to the plurality of positions from which the sets of data are obtained so that said plurality of sets of data can be used to create an image of said internal features at said site.

In accordance with another aspect of the present invention a method of imaging internal features of a living body at a preselected site is provided. The method comprises the steps of:

(a) partially inserting a catheter into said body so that the distal end of said catheter is positioned relative to said preselected site so that data relating to an image of said internal features can be acoustically sensed at said distal end by moving said distal end through a plurality of positions;

(b) collecting a corresponding plurality of sets of data derived from acoustic signals generated from said distal end of said catheter as said distal end is moved through said plurality of positions; and (c) relating the plurality of sets of data with respect to the plurality positions from which the sets of data are obtained so that said plurality of sets of data can be used to create a coherent image of said internal features at said site.

Other objects of the invention will in part be obvious and will in part appear hereinafter. The invention accordingly comprises the apparatus possessing the construction, combination of elements, and arrangement of parts which are exemplified in the following detailed disclosure, and the scope of the application of which will be indicated in the claims.

For a fuller understanding of the nature and objects of the present invention, reference should be had to the following detailed description taken in connection with the accompanying drawings, wherein.

Throughout the drawings the same numerals are used to describe the same or similar parts.

Figure 1:
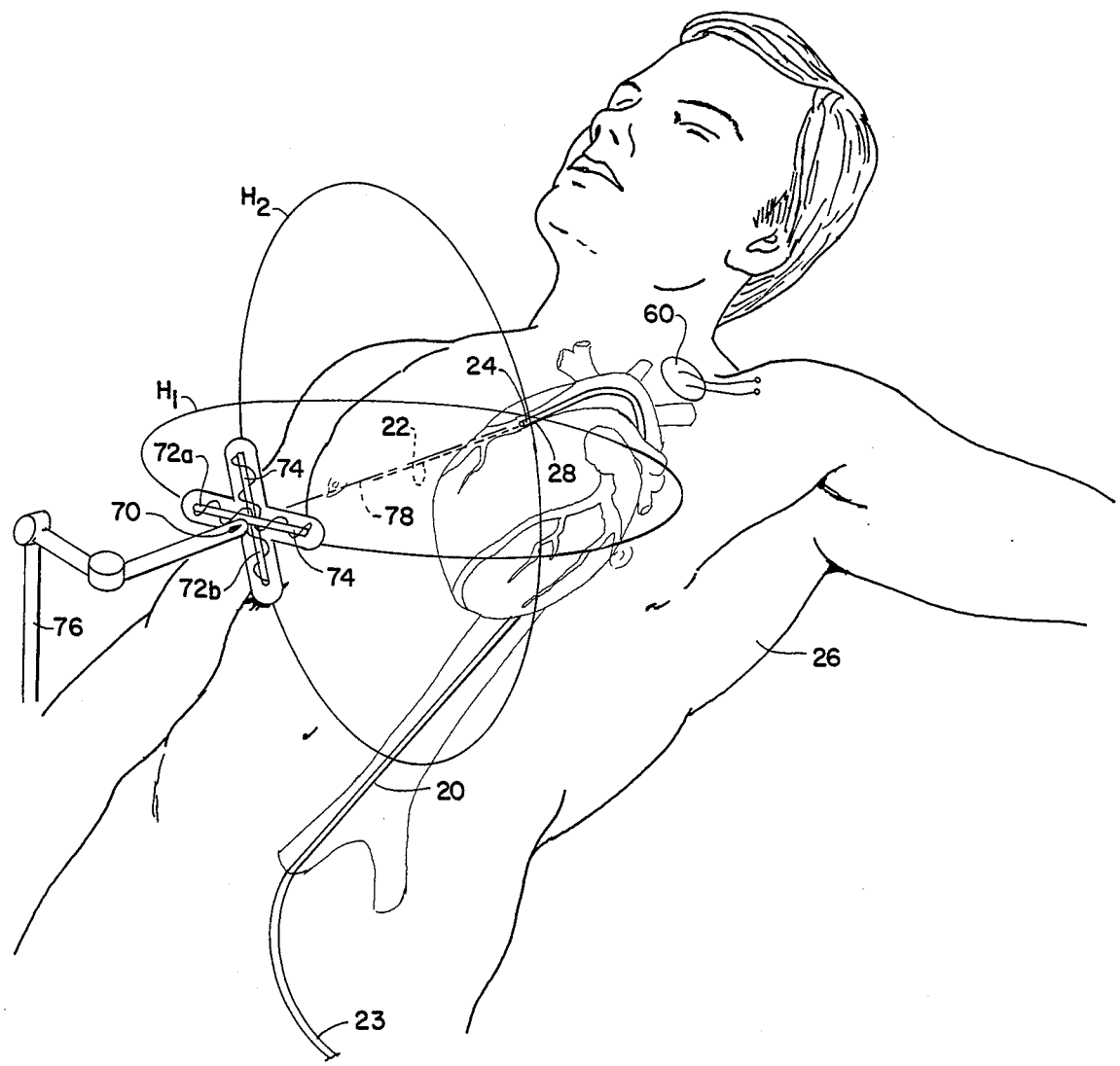
FIG. 1 is a perspective view of a portion of the catheter and the position sensing means of the preferred apparatus of the present invention in position for imaging the tissue at a particular diseased site of a living body.
Figure 2:
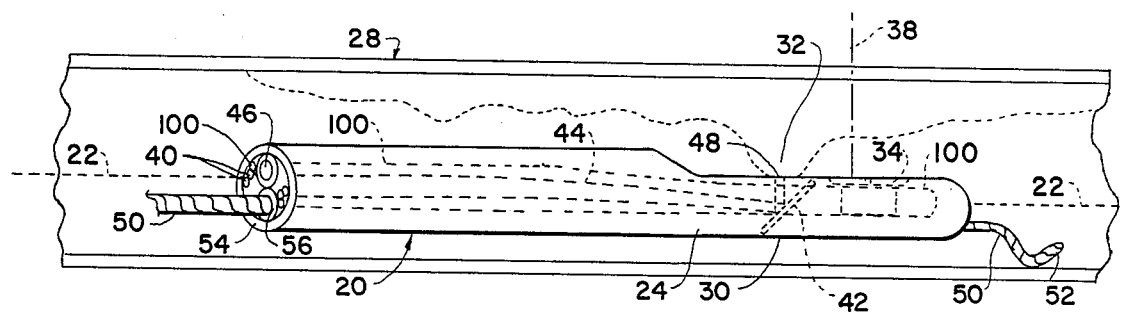
FIG. 2 is a side view, in phantom, of the distal end portion of the catheter shown in FIG. 1, showing the tip in position for imaging an atherosclerotic lesion.

Referring to FIGS. 1 and 2 the preferred apparatus for imaging internal features of a living body within a preselected site includes the catheter 20 having a longitudinal axis, designated generally at 22. The catheter includes a proximal end 23 and a distal end 24, and is adapted to be partially inserted into living body 26 so that the distal end 24 is positioned at a preselected location at or within a preselected site, such as coronary artery 28, while the proximal end 23 is positioned outside the body where it can be gripped by the physician. As shown in FIG. 1, the distal end 24 of catheter 20 is designed so that (1) it is capable of being positioned within portions of the coronary arteries, (2) it can image those portions for the presence of atherosclerotic lesions and (3) it can provide laser radiation for ablating the diseased tissue from the walls of those blood vessels. It should be appreciated, however, that the present invention can be used for imaging other portions of the body and need not be adapted to provide laser radiation to a particular site.

In FIG. 2, the catheter 20 is shown disposed within the artery 28 with the tip section 30 of the distal end 24 positioned opposite a portion of a stenotic lesion shown at 32. Electro-acoustical, transducer means 34, secured within the tip section 30, is positioned to transmit a beam of acoustical pulses from tip section 30, transversely to longitudinal axis 22 of catheter 20, in the general direction of an axis of propagation 38 (hereinafter also referred to as a "data sensing" or "imaging" axis for ease of exposition), in response to electrical pulses transmitted along the insulated electrical conductors 40, disposed within the catheter 20. The transducer means 34 can include a single transducer which is switched back and forth between a transmission mode and a receiving mode, but preferably includes a pair of distinct transducers, one connected for transmission, and the other for receiving, as generally described in the Parent Application. The acoustic pulses transmitted along axis 38 pass into the lesion 32 and the underlying arterial wall of the artery 28. Acoustical echoes, reflected by the impedance mismatches of the various surfaces of the different tissue back toward the transducer means, are reconverted by the transducer means 34 to electrical signals which are transmitted back along conductors 40 (in the case of a single transducer being used for both transmission and reception of acoustic energy), or along a separate pair of conductors 40a (in the case of a pair of transducers, one for transmission and the other for reception of acoustic energy. The acoustical echoes represent a set of data D at each position acoustical echoes are detected by the transducer means 34. These signals are used to, generate an image of the lesion and surrounding tissue.

Where laser radiation is used in conjunction with the imaging procedures, catheter tip section 30 also includes a mirror 42 that intercepts a laser beam 44 transmitted along the catheter through an optical waveguide 46, such as optical fibers made of a material having good transmissive properties at the frequency of the laser radiation. The mirror reflects beam 44 through a window 48 toward lesion 32. As constructed, the principal direction of beam 44, parallel to the axis 38, is extemely close to and displaced by a known distance from axis 38. A guide wire 50, extending through catheter 20, includes a spring-like tip portion 52 that lightly bears against the inner wall of artery 28, opposite the direction of axis 38 for positioning tip section 30 for efficient operation of the laser excision procedure. The catheter is encased in an outer sheath 54 which encloses, in addition to waveguide 46, (1) a tube 56 for guide wire 50 and (2) insulated electrical conductors 40 (and 40a). In addition, a wire loop 100 is disposed in outer sheath 54, the purpose of the loop being described hereinafter with respect to the description of FIG. 4. The specific technique of acquiring image data from the surrounding tissue at the site of distal end 24 of the catheter in connection with the simultaneous determination of the specific location of transducer means 34, and angular orientation of axis 38 (about longitudinal axis 22) will be described hereinafter.

In order to determine the specific location of transducer means 34 and angular orientation of axis 38, the apparatus of the present invention also comprises position sensing means for determining, externally of the body, the position of the transducer means within the body 26 and the angular orientation of the axis 38 about longitudinal axis 22. The position sensing means preferably includes (a) means, positioned outside the body, for generating reference signals at corresponding predetermined reference frequencies, (b) means positioned on the catheter and substantially fixed relative to the data sensing axis 38 for sensing each of the reference signals and (c) means for processing the signals received by the sensing means for determining the relative position of transducer means 34 and angular orientation of axis 38.

Preferably, as shown in FIG. 1, the means for generating the reference signals includes means, in the form of transducer 60, for generating an ultrasonic reference signal at a preselected frequency (indicated as $f_3$ in the drawings) for determining the position of the transducer means 34. The frequency $f_3$ of the ultrasonic signal should be high enough to easily propagate through the living body 26, and define a sufficiently long wavelength relative to the portion of the body to be imaged, e.g., a section of artery 28, so that phase differences can represent the relative positions of the transducer means within the portion of the body being imaged. For example, where a 2 cm section of coronary artery is to be imaged in increments of 0.5 mm, a satisfactory ultrasonic signal has a frequency of 100 KHz defining a wavelength of about 1.5 cm. Transducer 60 can easily be placed in position by taping, or otherwise securing the transducer directly to the outer skin of body 26, preferably near the area where the distal end 24 of the catheter 20 is located during the imaging procedure described hereinafter.

The means for generating the reference signals also includes an "electromagnetic radiation illuminator" 70 for transmitting a pair of reference fields in the direction of distal end 24 of catheter 20 and used for determining the angular orientation of data sensing axis 38 with respect to longitudinal axis 22. As shown in FIG. 1, illuminator 70 includes a pair of coils 72a and 72b, each wound about a separate core element 74 of magnetically conductive material, e.g., ferrite, so as to generate two alternating magnetic reference fields (indicated respectively as $H_1$ and $H_2$). The fields are preferably generated at two different frequencies, shown in the drawings as f and $f_2$ in planes transverse to one another, and preferably perpendicular to one another. Alternatively, the two fields can be generated at the same frequency but out of phase with one another. The frequencies $f_1$ and $f_2$ are chosen so that they are substantially large enough to be insensitive to interference from body motion, small enough to be insensitive to radio frequencies and yet within a range of frequencies so as to be easily detected by a relatively small antenna, preferably in the form of loop 100 positioned on the distal end 24 of the catheter, as shown and described hereinafer with respect to FIG. 4. Examples of $f_1$ and $f_2$ are 16 KHz and 20 KHz, respectively, although these frequencies can vary. Preferably, the coils 72a and 72b and core elements 74 are suitably supported (as for example on support 76) and oriented perpendicular to one another so that the planes of the fields are perpendicular to one another. The direction of the illuminator 70, as defined by the intersecting line 78 formed where the two planes $H_1$ and $H_2$ intersect, should be pointed toward the approximate position of the distal end 24 of catheter 20, substantially coaxial with the longitudinal axis 22 of the catheter at the distal end, although an angle of as much as 20° can be tolerated without substantially affecting the operation of the apparatus.

Figure 3:
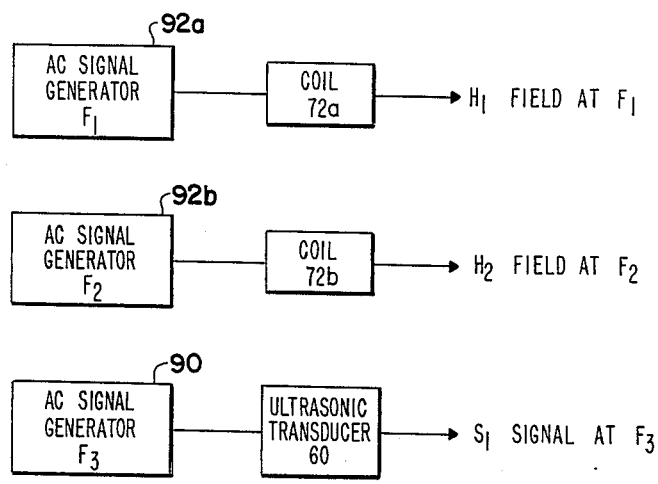
FIG. 3 is a block diagram of the system for generating the reference signals of the position sensing means of the preferred system of the present invention.

Referring to FIG. 3, the sonic signal $S_1$ can be generated by the signal generator 90. The latter is suitably connected to the transducer 60 and generates an AC signal at the frequency $f_3$. The fields $H_1$ and $H_2$ easily can be generated by connecting the coils 72a and 72b to respective signal generators 92a and 92b for generating AC signals at the respective frequencies $f_1$ and $f_2$.

Figure 4:
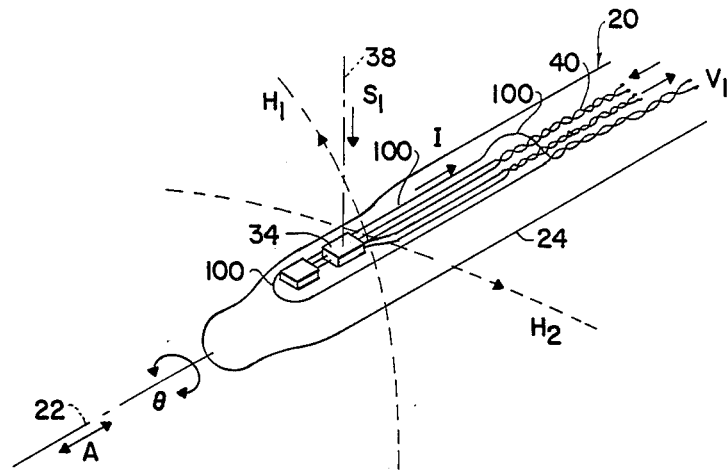
FIG. 4 is a perspective view of the distal end portion of the catheter shown in FIG. 1, showing details of the means for sensing the reference signals of the position sensing means of the preferred system of the present invention.

As best shown in FIG. 4, the means for sensing the sonic signal $S_1$ and the fields $H_1$ and $H_2$ is preferably provided by the transducer means 34 for sensing $S_1$ and the antenna wire loop 100 for sensing the $H_1$ and $H_2$ fields. Transducer means 34 is capable of receiving both the $S_1$ signal and the acoustic reflections from the sounding tissue in response to the acoustic, signals generated by the transducer means. The antenna wire loop 100 is shaped so as to sense the components of $H_1$ and $H_2$ passing through the plane of the loop. The loop 100 is made large enough to adequately sense the components of the fields, yet small enough to easily fit within the sheath 54, as well as to minimize any distortion created when the loop is bent out of its plane due to the flexing of catheter 20 at its distal end 24. An example of the dimensions of the loop are about 20 mm lengthwise (along the direction of longitudinal axis 22 of the catheter) and about 0.7 mm wide (at right angles to the longitudinal axis so as to define a reception area of about $14 \times 10^{-6}$ $m^2$. The transducer means 34 is preferably positioned within and fixed with respect to the loop, with the data sensing axis 38 extending normal to the plane of the loop so that the loop always remains substantially fixed with respect to the data sensing axis.

Figure 5:
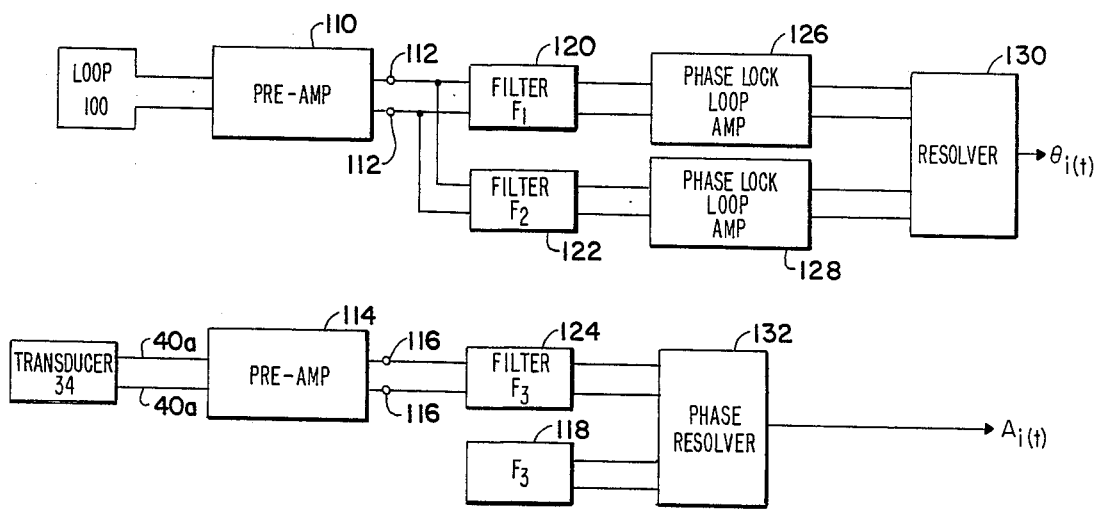
FIG. 5 is a block diagram of the means for processing the sensed reference signals of the position sensing means so as to generate position signals representative of the position of the catheter tip.

The reference signals provided by transducer 34 and loop 100 can easily be detected with the device shown in FIG. 5. As shown, the loop 100 is connected to a pre-amplifier 110, which in turn is connected to the terminals 112. The transducer means 34 is connected through conductors 40a to the pre-amplifier 114, which in turn is connected to the terminals 116. The signal at terminals 116 will include the echo data received by the transducer means as well as the detected reference signal $S_1$. The electrical signal provided at terminal 112 is a function of the components of the $H_1$ and $H_2$ field passing through the plane of the loop. As shown, the means for detecting the reference signals includes three filters 120, 122 and 124, respectively having very narrow passbands at $f_1$, $f_2$ and $f_3$. The output of filter 120 is applied to a phase lock loop amplifier 126, which in turn provides a signal representative of the component of the $H_1$ field sensed by the antenna loop 100. The component will be a function of the sine of the angle $\theta$ that the plane of the loop 100 makes with the plane of the $H_1$ field. Similarly, the output of filter 122 is applied to a phase lock loop amplifier 128, which in turn provides a signal representative of the component of the $H_2$ field sensed by the antenna loop. The component will be a function of the cosine of the angle that the plane of loop 100 makes with the plane of the $H_1$ field. Since the plane of the loop is substantially fixed with respect to axis 38, the relative angle $\theta$ of the data sensing axis 38 can be calculated with the resolver 130 from the values of field components in a manner well known in the art, as for example using arc tangent tables. The output value of resolver 130 will therefore be a signal representative of the value of $\theta_i(t)$, which, as previously indicated, provides the angle of data sensing axis 38 relative to the planes of the $H_1$ and $H_2$ fields.

In order to determine the location of the transducer means 34, the output of the filter 124 is applied to the phase resolver 132 which compares the phase of the signal generated by the transducer 60, as indicated at 118, and the signal provided by filter 124. Since the wavelength of the signal is relatively large (e.g. 1.5 cm) compared to the increments of the portion of the artery to be imaged (e.g., 0.5 mm increments), the relative measurement of phase will indicate the relative position of the transducer means 34, $A_i(t)$, as the transducer means is moved within the portion of the artery to be imaged.

Figure 6:
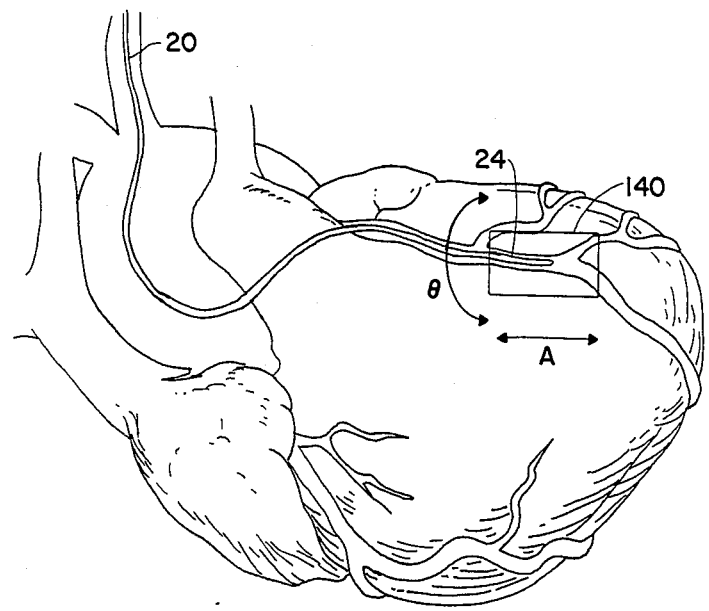
FIG. 6 is a view of the distal end of the catheter in position in the heart to illustrate ambient motion affecting the values of the position signals derived from the signal processing means illustrated in FIG. 5.

To the extent described, the values of $\theta_i(t)$ and $A_i(t)$ would provide suitable information as to the relative locations of the tissue represented by the sets of data $D_i(t)$, as the latter are received by the transducer means 34, if the environment in which the distal end of the catheter is positioned does not move during the time data is collected. However, at least in the case of gathering data from coronary arteries, the environment will move in a rhythmic motion as a result of the heart beating. For example, as shown in FIG. 6 where the distal end 24 of catheter 20 is positioned in a coronary artery within the block indicated at 140, both the value of A and $\theta$ will vary with the cycle of the heart beat, even if the catheter is not moved by the physician relative to the coronary arteries within which the distal end of the catheter is positioned. As a result in the preferred embodiment, means are provided for compensating for this "neighborhood" ambient rhythmic motion.

Figure 7:
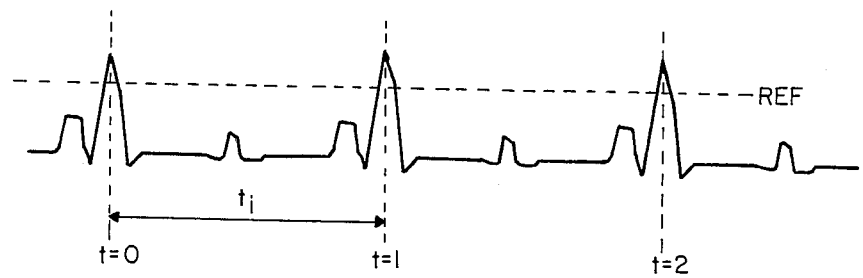
FIG. 7 is a simplified graphical representation of a typical heart beat.
Figure 8:
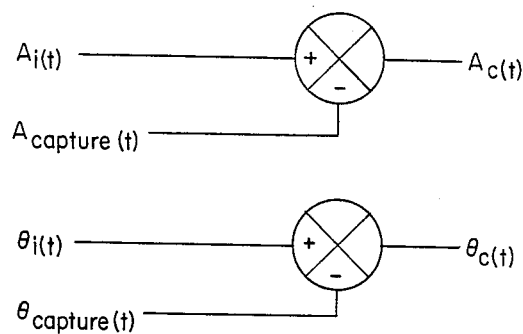
FIG. 8 is a simplified signal diagram showing additional signal processing necessary for eliminating the affect of ambient motion on the position signals.

As shown in FIG. 7, a simplified graph of a heart beat, as it might appear on an electrocardiograph, includes a systolic pulse shown at time $t=0$. For purposes of the present invention, the peak of this pulse is considered the beginning of each cycle of the heart beat, so that subsequent cycles commence at $t=1$, $t=2$, etc. In order to compensate for the neighborhood ambient rhythmic motion, the sensed motion of the transducer means 34 due to the neighborhood ambient motion associated with the heart beat, at the position where data is collected, must be subtracted from the detected values $\theta_i(t)$ and $A_i(t)$. This is preferably accomplished by moving the distal end of the catheter into the location where data is to be collected and initially allowing the distal end to move only in response to neighborhood ambient motion. The values of $\theta$ and A are then preferably measured over an entire cycle of the heart beat (hereinafter referred to as the "capture" cycle) so as to provide values of $\theta$ and A over the entire cycle, referred to as $\theta_{capture}(t)$ and $A_{capture}(t)$. As shown in FIG. 8, for each subsequent cycle that imaging data is collected, the values of $\theta_{capture}(t)$ and $A_{capture}(t)$ occuring over the capture cycle are subtracted from the corresponding values of $\theta_i(t)$ and $A_i(t)$ obtained in each subsequent cycle. The foregoing will become more evident hereinafter in connection with the description of FIGS. 9 and 10.

Figure 9:
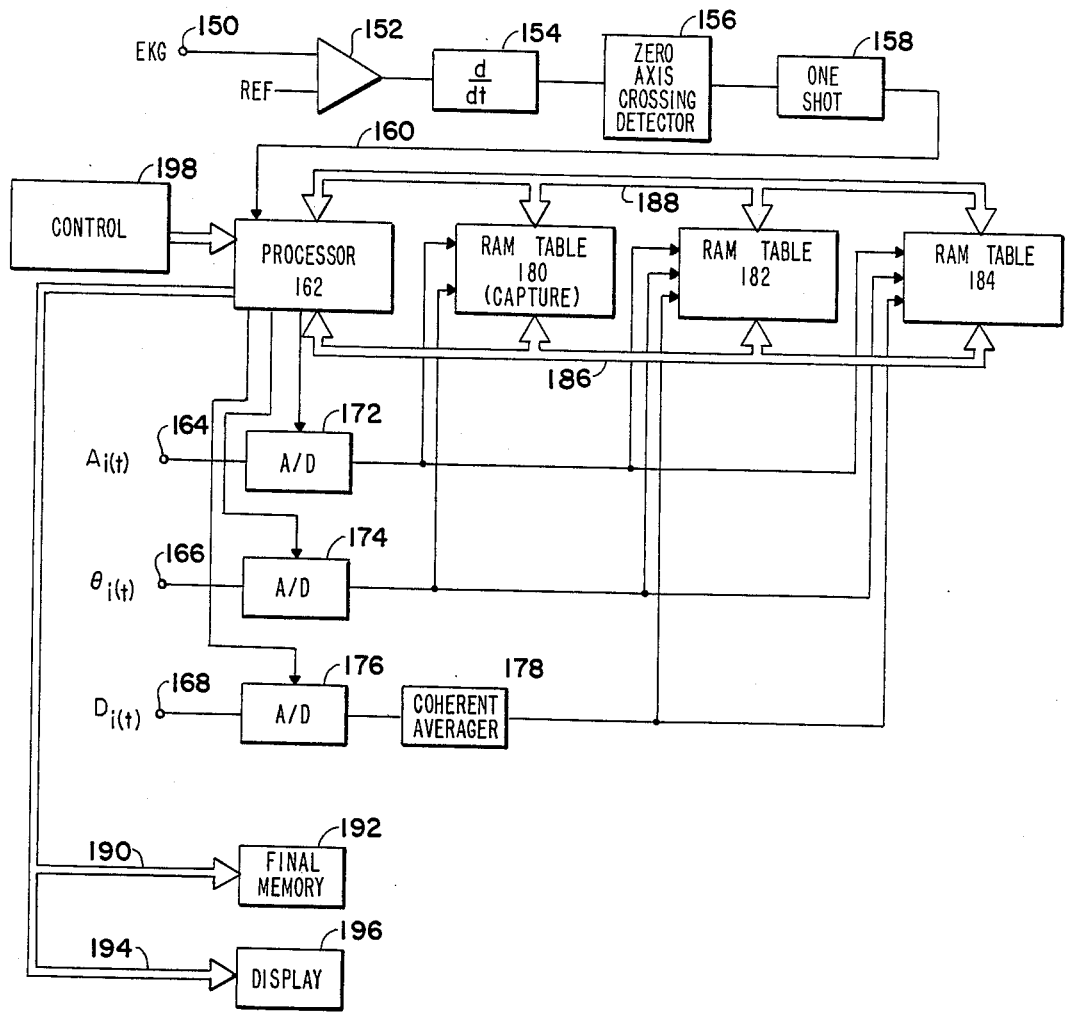
FIG. 9 is a block diagram of additional signal processing means for substantially eliminating the affect of ambient motion on the position signals.

Referring to FIG. 9, the system shown includes input 150 for receiving the EKG signal, similar to the one shown in FIG. 7. Input 150 is connected to suitable means for sensing the beginning of a heart cycle at $t=0$, $t=1$, $t=2$, etc. This can be accomplished by any suitable means known in the art. As shown, the EKG signal is applied to a threshold detector 152. The level of the reference input applied to detector 152 is less than the level of the peak of the systolic portion of the cycle, but greater than the remaining portion of the signal of the cycle, as for example, indicated by the reference line REF shown in FIG. 7.

The output of detector 152 is applied to the input of a signal differentiator 154 for generating a signal as a function of the derivative of the output signal of the detector 152. The output of differentiator 154 is in turn applied to the input of a zero axis crossing detector 156, the latter being adapted to detect when the peak of the systolic pulse occurs (i.e., the slope, and therefore the derivative is zero). When the slope is zero at time $t=0$, $t=1$, $t=2$, etc., detector 156 provides a signal to the one shot 158, which in turn indicates (on line 160) to the procesor 162 that a heart cycle has begun. Other devices are known for timing heart cycles, such as various heart monitoring equipment and can easily be adapted to provide a signal at the beginning of each heart cycle as herein defined.

The $A_i(t)$ and $\theta_i(t)$ signals respectively from the outputs of the resolvers 132 and 130 of FIG. 5 are applied to the inputs 164 and 166, shown in FIG. 9. The imaging data $D_i(t)$ is obtained from terminals 116 of FIG. 5 and applied to input 168, also shown in FIG. 9. The imaging data is collected at a rate substantially greater than the frequencies of any of the reference signals. Preferably, the imaging data is obtained by generating a burst of pulses every sampling period. The sampling period is set to about 40 per second, with a burst of, for example, 500 pulses being generated within each sampling period. The relative timing of the burst of pulses can be varied in accordance with a well known "pulse staggering" technique (where, for example, the period between successive pulses is increased until the burst is completed) so as to be better able to discriminate the echos returning to the transducer means 34. With this technique transducer means 34 preferably includes two transducers so that the data is continuously received. At this rate the data will be received at frequencies well above 100 KHz, the value of $f_3$. Accordingly, the signal provided at terminal 168 is applied to a high pass filter 170 adapted to pass signal energy above 100 KHz.

The $A_i(t)$ and $\theta_i(t)$ signals provided at terminals 164 and 166 and the image data signal $D_i(t)$ are respectively applied to analog-to-digital (A/D) converters 172, 174 and 176. The digital conversion rates of the A/D converters are each set by processor 162, with the conversion rate for converter 176 being set at about 20 MHz;

and the conversion rates of converters 172 and 174 each being set for 40 Hz, at least for the cycles following the capture cycle. The digital conversion rate of converters 172 and 174 during the capture cycle will depend upon the operation of processor 162, as will be more apparent hereinafter.

The output of the A/D converter 176 is connected to the input of a coherent averager 178, of a type well known in the art, for improving the signal-to-noise ratio of the digitized $D_i(t)$ output of the converter. The outputs of converters 172 and 174 are connected to inputs of each of the RAM (Random Access Memory) Tables 180, 182, and 184, while the output of coherent averager 178 is connected to additional input of RAM Tables 182 and 184.

Figure 11:
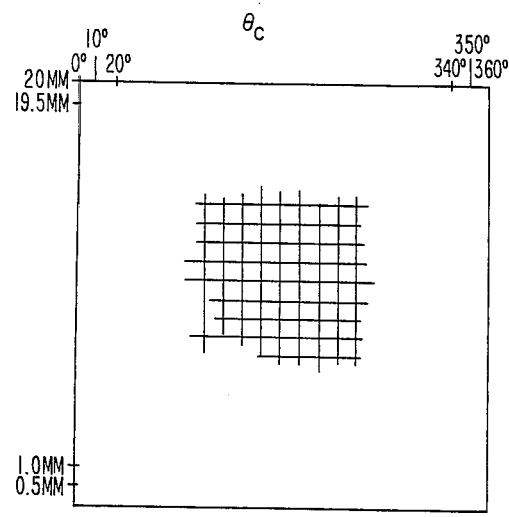
FIG. 11 shows a simplified version of a display of a imaged section of a coronary artery using the present invention.

RAM Table 180 stores the values of $A_{capture}$ and $\theta_{capture}$ taken during the capture cycle. RAM Tables 182 and 184 are utilized to store the values of $A_i(t)$, $\theta_i(t)$ and $D_i(t)$ for alternate cycles of the heart beat following the capture cycle. The read and write modes of RAM Tables 180, 182 and 184 are controlled by processor 162 through the lines 186. The corrected values of $A_c$ and $\theta_c$ are determined by processor 162 by retrieving the values of $A_i(t)$ and $\theta_i(t)$ and the correponding values of $A_{capture}$ and $\theta_{capture}$ over lines 188 from the stored values in RAM Tables 180 and 182, or 180 and 184, as will be more evident hereinafter. The values of $A_c$ and $\theta_c$ are determined by processor 162 and then transferred over lines 190 and stored with the corresponding values of $D_i(t)$ in the final memory 192. All or part of the data $D_i(t)$ for each set of $A_c$ and $\theta_c$ can then be transmitted over lines 194 and displayed on display 196. In this regard each pixel address of the display 196, as shown in FIG. 11, can be defined as the particular value of $A_c$ and $\theta_c$, and the intensity of the pixel at that address a function of all or part of the data $D_i$ obtained for those values of $A_c$ and $\theta_c$. Finally, external commands to the processor 162 can be entered by the physician through the control 198.

The foregoing will be more evident from the following description of the operation of the apparatus. The transducer 60 is secured in place and the illuminator 70 is pointed in the correct direction by pointing the intersecting line 78 toward the general vicinity of the body 26 where the distal end will be placed substantially aligned with the longitudinal axis of the catheter at the distal end. The distal end 24 of the catheter 20 is inserted into the living body and moved to the location to be imaged with the proximal end 23 within reach of or held by the physician. In this regard a fluoroscope can be used to bring the distal end 24 into proximity with the location to be imaged by the apparatus. Once the distal end 24 is positioned in the general area of interest, the physician energizes the signal generators 90 and 92 so as to generate the sonic signal $S_1$ and fields $H_1$ and $H_2$. The transducer 34 will sense the signal S and loop 100 will sense the components of the fields H and H passing normal through the plane of the loop. The reference signals will be processed and values of $\theta_i(t)$ and $A_i(t)$ will be provided at the outputs of the resolvers 130 and 132.

Figure 10:
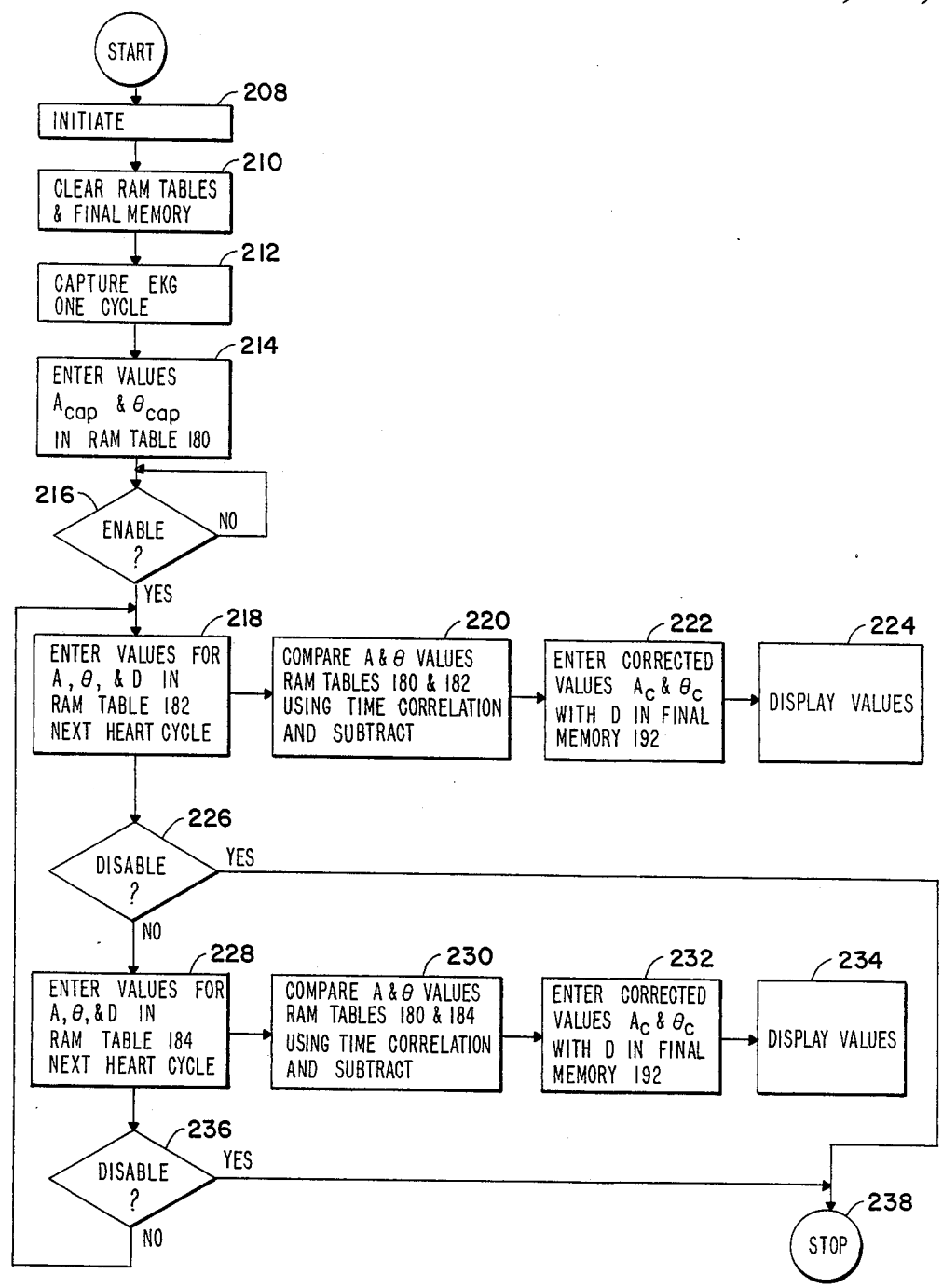
FIG. 10 is a flow chart of the operation of the signal processing means shown in FIG. 9.

The physician is now ready to run a capture cycle. As shown in FIGS. 9 and 10, when the physician enters an initiate signal through control 198 at step 208, the RAM Tables 180, 182 and 184 and final memory 192 are cleared at step 210. Processor 162 is then enabled to process the values of $A_{capture}(t)$ and $\theta_{capture}(t)$, as indicated at step 212. $A_i(t)$ and $\theta_i(t)$, providing the values of $A_{capture}$ and $\theta_{capture}$ during the capture cycle, are applied respectively at inputs 164 and 166 during a cycle of the rhythmic ambient motion, as indicated at step 214. During this cycle the catheter is not moved by the physician. The capture cycle will commence at t=0 and end at t=1. $A_i(t)$ and $\theta_i(t)$ are digitized at a conversion rate determined by processor 162. The conversion rate can be same a the conversion rate of $A_i(t)$ and $\theta_i(t)$ during subsequent cycles, or at a much faster rate in order to capture a rich sampling of values during the capture cycle. For example, where the converters 180 and 182 digitally convert the values of $A_i$ and $\theta_i$ during subsequent cycles at a rate of 40 Hz, the conversion rate during the capture cycle can be 1 KHz. Since the catheter is not moved during the intiation cycle and the average resting heart rate is between 60 and 72 beats per minute, the capture cycle will take between about 0.83 and 1.00 seconds to complete. This will result in about 830 to a 1000 samples being taken during the capture cycle, representative of the movement of the distal end of the catheter during a cycle of the heart beat. These values of $A_i$ and $\theta_i$ represent $A_{capture}$ and $\theta_{capture}$ for the capture cycle and are stored in RAM Table 180, as indicated at step 214. The latter is accomplished by enabling RAM Table 180 in the Write mode during the capture cycle so that the outputs of converters 172 and 174 are written directly into memory.

Where, for example, 1000 samples are taken the values in Table 180 are listed as follows:

TABLE 180

| Sample | $A_{capture}$ | $\theta_{capture}$ |
|---|---|---|
| 1 | $A_1$ | $\theta_1$ |
| 2 | $A_2$ | $\theta_2$ |
| . | . | . |
| . | . | . |
| . | . | . |
| 1000 | $A_{1000}$ | $\theta_{1000}$ |

With the values of $A_{capture}$ and $\theta_{capture}$ in memory, the physician now can provide an enable signal through control 198, as indicated at step 216 in FIG. 10. During this time it may, be preferred to have the patient hold his or her breath so as to slow the heart rate. During the next full cycle of the heart, the pulses provided to transducer means 34 (which in turn are converted to acoustic pulses propagated in the general direction of axis 38), can be provided by processor 162 at the required rate. The returned echoes are sensed by the transducer means 34 and transmitted to the input 168 (of FIG. 9) as the set of data, $D_i(t)$. The set of data acquired during each sampling period, determined by the conversion rate applied by processor 162 to the A/D converters 172 and 174, will be applied to the inputs of RAM Table 182 along with the value of $A_i(t)$ and $\theta_i(t)$ for that sampling period. As previously mentioned the preferred conversion rate of converters 80 and 182 during these cycles is 40 Hz so that if a subsequent heart cycle takes one second, 40 sets of data $D_i(t)$ will be read into RAM Table 182 along with the corresponding digitized values of $A_1(t)$ and $\theta_i(t)$ for each set. If the heart cycle takes 1.1 seconds, 44 samples will be read into memory, etc.

Where, for example, 40 samples are taken, the values in Table 182 are listed as follows:

TABLE 182

| Sample | $A_i$ | $\theta_i$ | $D_i$ |
|---|---|---|---|
| 1 | $A_i$ | $\theta_1$ | $D_1$ |
| 2 | $A_2$ | $\theta_2$ | $D_2$ |

TABLE 182-continued

| Sample | $A_i$ | $\theta_i$ | $D_i$ |
|---|---|---|---|
| . | . | . | . |
| . | . | . | . |
| . | . | . | . |
| 40 | $A_{40}$ | $\theta_{40}$ | $D_{40}$ |

The processor 162 proceeds to step 220, wherein the values in RAM Tables 180 and 182 are read into the processor 162 so that the appropriate values of $A_{capture}$ and $\theta_{capture}$, taken from the samples $A_{capture}(t)$ and $\theta_{capture}(t)$ contained in RAM Table 180 and representative of the ambient motion at the time in the heart cycle at which each of the sample values are obtained, can be subtracted from the corresponding values of $A_i$ and $\theta_i$ taken from RAM Table 182. In the example given, where 40 samples are taken during a subsequent heart cycle, the values of $A_{c1}$ and $\theta_{c1}$ are obtained by subtracting the values of $A_{capture}$ and $\theta_{capture}$ of the 25th sample of the capture cycle, from the values of $A_1$ and $\theta_1$ of the first sample of the subsequent cycle stored in RAM Table 182. Similarly, the values of $A_{c2}$ and $\theta_{c2}$ are obtained by subtracting the values of $A_{capture}$ and $\theta_{capture}$ of the 50th sample of the capture cycle from the values of $A_2$ and $\theta_2$ of sample 2 stored in RAM Table 182. The process continues with values of $A_c$ and $\theta_c$ being determined from each successive sample of $A_i$ and $\theta_i$ and the corresponding sample of the captured values of $A_{capture}$ and $\theta_{capture}$ at successive 25th intervals, since the latter values correspond to the values of A and $\theta$ at the relative time positions of the 40 samples taken in the subsequent data gathering heart cycle. The results of each correction are written with the corresponding values of $D_i$ into final memory 192, as indicated at step 222.

Where, for example, 40 samples were taken and corrected, the values entered into final memory 192 are listed as follows:

TABLE 192

| Sample | $A_{ci}$ | $\theta_{ci}$ | $D_i$ |
|---|---|---|---|
| 1 | $A_{ci}$ | $\theta_{c1}$ | $D_1$ |
| 2 | $A_{c2}$ | $\theta_{c2}$ | $D_2$ |
| . | . | . | . |
| . | . | . | . |
| . | . | . | . |
| 40 | $A_{c40}$ | $\theta_{c40}$ | $D_{40}$ |

Figure 12:
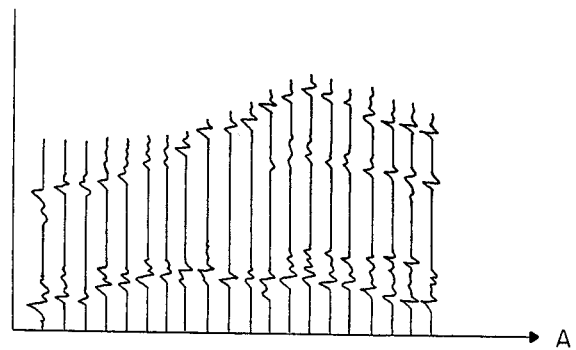
FIG. 12 is a series of echograms at selected positions of a diseased site acquired in accordance with the present invention.

It should be noted that the values of $D_i$ remain unchanged. If $A_c$ is incremented in 0.5 mm increments and $\theta_c$ is incremented in 10 degree increments each set of data can be displayed, as indicated at step 224, as a pixel having an address $A_c$ by $\theta_c$ on display 196 (see FIG. 11) having a 36×40 pixel array representative of a 360° by 2 cm area. The intensity of each pixel can be a function of all or part of the data $D_i$ at that location. For example, the intensity can represent the thickness of plaque, the density of the plaque, etc. The physician can control what the intensity of each pixel represents through control 198. Alternatively, one or more "echograms" (each echogram being a waveform detected by the transducer means 34 relating to $D_i$ at a particular location identified by $A_c$ and $\theta_c$) can be displayed, in a manner for example, as shown in FIG. 12. Displaying, for example, the echograms for all values of $A_c$ for a fixed value of $\theta_c$ will give a detailed characterization along a longitudinal line down the section of coronary artery at a particular fixed angle.

In the above example, while the samples of $A_{capture}$ and $\theta_{capture}$ used in step 220 to calculate the values of $A_c$ and $\theta_c$ directly correspond in the cycle time to values of the samples $A_i$ and $\theta_i$ during the subsequent cycle (at a ratio of 25:1), sampling during other cycles may not provide a direct correlation. Accordingly, a correlation algorithm of a type well known in the art can be utilized in processor 162 to correlate the closest value of $A_{capture}$ and $\theta_{capture}$ in the cycle time of the capture cycle to the time of the sample $A_i$ and $\theta_i$. In addition, or in the alternative, an interpolation algorithm of a type well known can be used to estimate the values of $A_{capture}$ and $\theta_{capture}$ for the precise time of the cycle needed, from the known values of $A_{capture}(t)$ and $\theta_{capture}(t)$, in order to calculate the values of $A_c$ and $\theta_c$ at the precise time of the cycle.

As shown at step 226, the processor 162 proceeds while carrying out steps 220, 222 and 224 by checking to see if the physician has removed the enable signal. If so, the processor 162 proceeds to the end 238 allowing steps 220, 222 and 224 to complete. If the enable signal is still indicated by the physician, the processor proceeds to steps 228, 230, 232 and 234. These steps are identical to steps 218, 220, 222 and 224, except that the values of $A_i(t)$ and $\theta_i(t)$ are written into RAM Table 184 during step 228 and read from that RAM Table during step 230. The processor then proceeds to step 236 to see if the enable signal has been released by the physician. If yes, the processor proceeds to the end 238. If no, the processor proceeds back to step 218 and repeats steps 218, 220, 222 and 224. The program continues through the loop of steps 218 (which results in steps 220, 222 and 224), 226, 228 (which results in steps 230, 232 and 234) and 236 until the physician withdraws the enable switch. When the latter occurs the processor will proceed to step 238 the next time processor performs step 226 or 236.

The enable signal is depressed by the physician as long as he or she desires, with 15 seconds being typical. At the rate of 40 samples per second, this will result in as many as 600 samples. During this time the catheter is manipulated by the physician by twisting and longitudinally moving the distal end of the catheter within the 2 cm and 360° area, with the results displayed on display 196. Any duplicated samples taken from the same incremental area represented by a single pixel will simply be processed and the results written over the previous values taken at that location. The display can also display the current location of the imaging axis, as well as provide the constant update of data as it is acquired. In this way the physician can easily move the distal end of the catheter into an area where data is needed by looking at the display during the sampling time to see which pixel areas have insufficient data.

The foregoing provides a system for and method of collecting sets of data derived from acoustic signals generated at a corresponding plurality of locations at or with a predetermined site of a living body, and relating the sets of data with respect to the relative locations from which the sets of data are obtained so that the data can be used to create a coherent image of the site. The system and method acquire ultrasonic echo data so as to create a relatively high resolution image in a quick and dependable manner. The system and method determine the relative position of the tip of a catheter within a living body, as well as the relative angular orientation of transducer device positioned on the tip of the catheter about the longitudinal axis of the catheter so as to provide information (a cyclindrical coordinate system) for creating a coherent image both in a longitudinal and angular direction.

Since certain changes may be made in the above apparatus and method without departing from the scope of the invention herein involved, it is intended that all matter contained in the above description or shown in the accompanying drawings shall be interpreted in an illustrative and not in a limiting sense.

What is claimed is:

1. Apparatus for sensing imaging information of the internal features of a living body at a preselected site, said apparatus comprising:

a catheter having a longitudinal axis, a proximal end and a distal end such that said catheter is adapted to be partially inserted into said living body so that said distal end is positioned relative to said preselected site so that said imaging information of said internal features can be acoustically sensed at said distal end;

image data sensing means, coupled to said catheter at said distal end, for acoustically sensing said imaging information of said body in the general direction of an image data sensing axis transverse to the longitudinal axis of said catheter at said distal end so that rotation of said catheter about said longitudinal axis rotates said image data sensing axis about said longitudinal axis; and position sensing means for determining the spatial position of said image data sensing means within said body and the angular orientation of said image data sensing axis about said longitudinal axis with respect to said spatial position so that imaging information of said body sensed by said image data sensing means at each such spatial position and angular orientation can be related to a specific cylindrical coordinate position, and imaging information of said body for a plurality of said cylindrical coordinate positions can be spatially cross correlated.

2. Apparatus according to claim 1, wherein said image data sensing means includes transducer means for generating an acoustic signal in the general direction of said image data sensing axis into said body and receiving echo signals reflected by said body in the general direction of said imaging axis in response to said acoustic signal.

3. Apparatus according to claim 2, wherein said transducer means includes a transmitter transducer for generating said acoustic signal and a receiver transducer for receiving said echo signals.

4. Apparatus according to claim 2, wherein said transducer means includes (a) a single transducer operable in a transmitting mode for generating said acoustic signal and a receiving mode for receiving said echo signals, and (b) means for operating said transducer in either said transmitting or said receiving mode.

5. Apparatus according to claim 2, further including means for generating said acoustic signal as a burst of pulses.

6. Apparatus according to claim 2, further including means for generating said acoustic signal as a burst of pulses staggered with respect to one another.

7. Apparatus according to claim 1, wherein said position sensing means includes first means for determining the spatial location of said imaging means within said body and second means for determining said angular orientation.

8. Apparatus according to claim 7, wherein said first means includes (a) transducer means for generating an acoustic signal toward said distal end of said catheter, and (b) means, coupled to said catheter at said distal end, for sensing said acoustic signal.

9. Apparatus according to claim 8, wherein said transducer means for generating said acoustic signal includes means for generating said acoustic signal at a preselected frequency.

10. Apparatus according to claim 9, wherein said means for sensing said acoustic signal includes antenna means coupled to said catheter at said distal end fixed relative to said imaging axis for generating a position signal in response to and as a function of the acoustic signal.

11. Apparatus according to claim 7, wherein said second means includes (a) means for generating two magnetic fields in two respective planes generally transverse to one another and (b) means, coupled to said catheter at said distal end, for sensing said magnetic fields.

12. Apparatus according to claim 11, wherein said first means includes (a) transducer means for generating an acoustic signal toward said distal end of said catheter, and (b) means, coupled to said catheter at said distal end, for sensing said acoustic signal.

13. Apparatus according to claim 11, wherein said means for generating said two magnetic fields includes means for generating each of said magnetic fields at a predetermined frequency, and said means for sensing said magnetic fields includes antenna mean coupled to said catheter at said distal end and fixed relative to said imaging axis for generating a position signal in response to and as a function of the magnetic fields.

14. Apparatus according to claim 13, wherein said antenna means includes a wire loop secured to said catheter and dimensioned so as to sense said magnetic fields at each of said predetermined frequencies and oriented so as to lie substantially in a plane fixed relative to said image data sensing axis.

15. Apparatus according to claim 14, wherein said wire loop is oriented so as to substantially lie in a plane fixed relative to said image data sensing axis.

16. Apparatus according to claim 13 wherein said means for generating each of said magnetic field includes means for generating said magnetic fields at different frequencies from one another, and said position sensing means includes means for sensing said position signal at each of said predetermined frequencies.

17. Apparatus according to claim 13, wherein said means for generating each of said magnetic fields includes means for generating said magnetic fields at the same frequency but out of phase with one another.

18. Apparatus according to claim 17, wherein said position sensing means includes means for sensing said position signal at said frequency.

19. Apparatus according to claim 1, wherein said position sensing means includes means for compensating for rhythmic ambient motion.

20. Apparatus according to claim 19, wherein said position sensing means includes (a) means for generating at least two position signals as a function of the position of said image data sensing means within said body and the angular orientation of said image data sensing axis about said longitudinal axis, (b) means for generating at least two second signals as a function of the movement of said image data sensing means in response to said rhythmic ambient motion for at least one cycle, and (c) means for subtracting said second signals from the corresponding ones of said position signals during each subsequent cycle of said rhythmic ambient motion.

21. Apparatus according to claim 20, wherein the cycle of said rhythmic ambient motion is variable, and said means for subtracting said second signals from said corresponding position signals is adapted to correlate the values of said second signals at their respective times of said at least one cycle, with the values of said position signals at the same corresponding times of each of said subsequent cycles.

22. Apparatus according to claim 1, further including means for spatially correlating the imaging information of said body sensed at a plurality of said cylindrical coordinate positions.

23. Apparatus for imaging internal features of a living body at a preselected site, said apparatus comprising, in combination:
a catheter having a longitudinal axis, a proximal end and a distal end such that said catheter is adapted to be partially inserted into said living body so that said distal end is positioned relative to said preselected site and imaging data relating to said internal features can be acoustically provided at said distal end by moving said distal end through a plurality of positions relative to said site and generating an acoustic signal when said distal end is at each of said positions;
means for selectively generating said acoustic signal when said distal end is at each of said positions;
first sensing means for sensing acoustic energy in response to said acoustic signal at each of said positions;
second sensing means for sensing the location of said distal end of said catheter at each of said positions;
means, responsive to said first and second sensing means, for collecting a set of data derived from the acoustic energy sensed by said sensing means at each of said positions and corresponding information relative to the corresponding position from which each set of data is obtained so as to form a plurality of said sets corresponding to a plurality of said positions; and
means for relating the plurality of sets of data with respect to the plurality of positions from which the sets of data are obtained so that said plurality of sets of data can be used to create an image of said internal features at said site.

24. Apparatus according to claim 23, wherein said first and second sensing means includes transducer means for generating said acoustic signal in the general direction of an image data sensing axis into said body at each of said positions, and receiving echo signals reflected by said body in the general direction of said image data sensing axis in response to said acoustic signal.

25. Apparatus according to claim 24, wherein said transducer means includes a transmitter transducer for generating said acoustic signal and a receiver transducer for receiving said echo signals.

26. Apparatus according to claim 24, wherein said transducer means includes (a) a single transducer operable in a transmitting mode for generating said acoustic signal and a receiving mode for receiving said echo signals, and (b) means for operating said transducer in either said transmitting or said receiving mode.

27. Apparatus according to claim 24, further including means for generating said acoustic signal as a burst of pulses.

28. Apparatus according to claim 24, further including means for generating said acoustic signal as a burst of pulses staggered with respect to one another.

29. Apparatus according to claim 24, wherein said image data sensing axis is transverse to the longitudinal axis of said catheter at said distal end, and said second sensing means includes first means for determining the spatial location of said second sensing means within said body, and second means for determining the angular orientation of said image data sensing axis about said longitudinal axis at said distal end.

30. Apparatus according to claim 29, wherein said first means includes (a) transducer means for generating an acoustic signal toward said distal end of said catheter, and (b) means, coupled to said catheter at said distal end, for sensing said acoustic signal.

31. Apparatus according to claim 30, wherein said transducer means for generating said acoustic signal includes means for generating said acoustic signal at a preselected frequency.

32. Apparatus according to claim 31, wherein said means for sensing said acoustic signal includes antenna means coupled to said catheter at said distal end and fixed relative to said imaging axis for generating a position signal in response to and as a function of the acoustic signal.

33. Apparatus according to claim 29, wherein said second means includes (a) means for generating two magnetic fields in two respective planes generally transverse to one another and (b) means, coupled to said catheter at said distal end, for sensing said magnetic fields.

34. Apparatus according to claim 33, wherein said first means includes (a) transducer means for generating a second acoustic signal toward said distal end of said catheter, and (b) means, coupled to said catheter at said distal end, for sensing said second acoustic signal.

35. Apparatus according to claim 33 wherein said means for generating said magnetic fields includes means for generating each of said magnetic fields at a predetermined frequency, and said means for sensing said magnetic fields includes antenna means coupled to said catheter at said distal end and fixed relative to said imaging axis for generating a position signal in response to and as a function of the magnetic fields.

36. Apparatus according to claim 35, wherein said antenna means includes a wire loop secured to said catheter and dimensioned so as to sense said magnetic fields at each of said predetermined frequencies and oriented so as to lie substantially in a plane fixed relative to said image data sensing axis.

37. Apparatus according to claim 35, wherein said means for generating each of said magnetic fields including means for generating said magnetic fields at different frequencies from one another, and said position sensing means includes means for sensing said position signal at each of said predetermined frequencies.

38. Apparatus according to claim 35, wherein said means for generating each of said magnetic fields includes means for generating said magnetic fields at the same frequency but out of phase with one another.

39. Apparatus according to claim 38, wherein said position sensing means includes means for sensing said position signal at said frequency.

40. Apparatus according to claim 23, wherein said second sensing means includes means for compensating for rhythmic ambient motion.

41. Apparatus according to claim 40, wherein said second sensing means includes (a) means for generating at least two position signals as a function of the position and orientation of said distal end within said body, (b) means for generating at least two second signals as a function of the movement of said image data sensing means in response to said rhythmic ambient motion for at least one cycle, and (c) means for subtracting said second signals from the corresponding ones of said position signals during each subsequent cycle of said rhythmic ambient motion.

42. Apparatus according to claim 23, wherein said wire loop is oriented so as to substantially lie in a plane fixed relative to said image data sensing axis.

43. A method of imaging internal features of a living body at a preselected site, said method comprising the steps of:
   (a) partially inserting a catheter into said body so that the distal end of said catheter is positioned relative to said preselected site so that data relating to an image of said internal features can be acoustically sensed at said distal end by moving said distal end through a plurality of positions;
   (b) collecting a corresponding plurality of sets of data derived from acoustic signals generated from said distal end of said catheter as said distal end is moved through said plurality of positions; and
   (c) relating the plurality of sets of data with respect to the plurality of positions from which the sets of data are obtained so that said plurality of sets of data can be used to create a coherent image of said internal features at said site.

44. A catheter assembly for use with a device for generating two magnetic fields in two respective planes generally transverse to one another, said assembly comprising:
   a catheter including a longitudinal axis, a proximal portion and a distal portion such that said catheter is adapted to be partially inserted into a living body so that the distal portion is positioned relative to a preselected site;
   means, positioned at said distal portion of said catheter, for (a) generating a beam of acoustic energy in a predetermined direction transverse to said longitudinal direction at said distal end so that the beam can be generated into said living body at said site, (b) sensing acoustic energy reflected by said body part along a image data sensing axis in response to said beam, and (c) generating an electrical signal in response to said and as a function of said sensed acoustic energy; and
   antenna means, positioned at said distal end of said catheter and fixed relative to the direction of said image data sensing axis, for sensing said magnetic fields and for generating an electrical signal representative of the spatial angular orientation of the direction of said image data sensing axis about said longitudinal axis relative to said distal end.

45. A catheter assembly according to claim 44, wherein said antenna means includes a wire loop (1) positioned at said distal portion of said catheter (2) substantially disposed in a plane fixed relative to the direction of said image data sensing axis, and (3) dimensioned so as to sense said magnetic fields.

46. A catheter assembly according to claim 45, wherein said wire loop is positioned at said distal portion so that the direction of said image data sensing axis extends through said wire loop.

47. A catheter assembly according to claim 46, wherein said wire loop is substantially disposed in a plane extending substantially normal to the direction of said image data sensing axis.

48. A catheter assembly according to claim 44, further including means, coupled to said catheter, for generating an electrical signal representative of the spatial position of said distal portion of said catheter.

* * * * *

UNITED STATES PATENT AND TRADEMARK OFFICE
CERTIFICATE OF CORRECTION

PATENT NO. : 4,821,731

DATED : April 18, 1989

INVENTOR(S) : Michael A. Martinelli and Peter von Thuna

It is certified that error appears in the above-identified patent and that said Letters Patent is hereby corrected as shown below:

Column 2, line 13, delete "which";

Column 2, line 59, after "as" insert -- to --;

Column 4, line 57, delete "earth" and substitute therefor -- each --;

Column 6, line 1, delete "a" and substitute therefor -- an --;

Column 12, line 43, after "may" delete -- , --.

Claim 10, column 16, line 12, after "end" insert -- and --;

Claim 13, column 16, line 31, delete "mean" and substitute therefor -- means --;

Claim 16, column 16, line 45, delete "field" and substitute therefor -- fields --;

Claim 23, column 17, line 27, after "of" insert -- three dimensional coordinate --;

Claim 23, column 17, line 29, after "said" insert -- three dimensional coordinate --;

Claim 23, column 17, line 31, after "said" (second occurrence) insert -- three dimensional coordinate --;

UNITED STATES PATENT AND TRADEMARK OFFICE
CERTIFICATE OF CORRECTION

PATENT NO. : 4,821,731

DATED : April 18, 1989

INVENTOR(S) : Michael A. Martinelli and Peter von Thuna

It is certified that error appears in the above-identified patent and that said Letters Patent is hereby corrected as shown below:

Claim 23, column 17, line 34, before "positions" insert -- three dimensional coordinate --;

Claim 23, column 17, line 36, after "said" (second occurrence) insert -- three dimensional coordinate --;

Claim 23, column 17, line 40, after "said" insert -- three dimensional coordinate --;

Claim 23, column 17, line 44, after "said" insert -- three dimensional coordinate --;

Claim 23, column 17, line 46, after "of" insert -- three dimensional coordinate --;

Claim 24, column 17, line 54, after "said" insert -- three dimensional coordinate --;

Claim 43, column 19, line 27, after "of" insert -- three dimensional coordinate --;

Claim 43, column 19, line 33, after "of" (first occurrence) insert -- three dimensional coordinate --;

Claim 44, column 20, line 12, delete "a" and substitute therefor -- an --;

UNITED STATES PATENT AND TRADEMARK OFFICE
CERTIFICATE OF CORRECTION

PATENT NO.  : 4,821,731

DATED       : April 18, 1989

INVENTOR(S) : Michael A. Martinelli and Peter von Thuna

It is certified that error appears in the above-identified patent and that said Letters Patent is hereby corrected as shown below:

Claim 44, column 20, line 14, delete "said" (first occurrence); and

Claim 45, column 20, line 25, after "catheter" insert -- , --.

Signed and Sealed this

Eleventh Day of February, 1992

Attest:

HARRY F. MANBECK, JR.

*Attesting Officer*      *Commissioner of Patents and Trademarks*